US009282985B2

(12) United States Patent
Finkman et al.

(10) Patent No.: US 9,282,985 B2
(45) Date of Patent: Mar. 15, 2016

(54) AIMING BEAM DETECTION FOR SAFE LASER LITHOTRIPSY

(71) Applicant: GYRUS ACMI, INC., Southborough, MA (US)

(72) Inventors: Shai Finkman, Haifa (IL); Adi Navve, Kfar Saba (IL)

(73) Assignee: GYRUS ACMI, INC., Southborough, MA (US)

(*) Notice: Subject to any disclaimer, the term of this patent is extended or adjusted under 35 U.S.C. 154(b) by 137 days.

(21) Appl. No.: 14/076,314

(22) Filed: Nov. 11, 2013

(65) Prior Publication Data

US 2015/0133728 A1   May 14, 2015

(51) Int. Cl.
| A61B 1/04 | (2006.01) |
| A61B 17/22 | (2006.01) |
| A61B 18/26 | (2006.01) |
| A61B 1/045 | (2006.01) |
| A61B 1/07 | (2006.01) |
| A61B 1/307 | (2006.01) |
| A61B 1/00 | (2006.01) |
| A61B 1/05 | (2006.01) |

(Continued)

(52) U.S. Cl.
CPC .......... *A61B 17/2202* (2013.01); *A61B 1/00009* (2013.01); *A61B 1/045* (2013.01); *A61B 1/05* (2013.01); *A61B 1/07* (2013.01); *A61B 1/307* (2013.01); *A61B 18/26* (2013.01); *A61B 18/24* (2013.01); *A61B 2017/22025* (2013.01); *A61B 2018/00505* (2013.01); *A61B 2018/00511* (2013.01); *A61B 2018/00642* (2013.01); *A61B 2018/1861* (2013.01); *A61B 2018/2035* (2013.01); *A61B 2019/5206* (2013.01)

(58) Field of Classification Search
USPC ......................................... 600/108; 606/2–16
See application file for complete search history.

(56) References Cited

U.S. PATENT DOCUMENTS

| 4,316,467 A * | 2/1982 | Muckerheide ................... 606/9 |
| 4,669,483 A | 6/1987 | Hepp et al. |

(Continued)

FOREIGN PATENT DOCUMENTS

| CA | 2362332 A1 | 8/2000 |
| CN | 1515231 A | 7/2004 |

(Continued)

OTHER PUBLICATIONS

ELMED Lithotripsy Systems, VIBROLITH PLUS, Intracorporeal Ultrasonic Plus Pneumatic Lithotripter with Integrated Adjustable Suction Device, 4 pages, Dec. 3, 2008.

(Continued)

*Primary Examiner* — Matthew J Kasztejna
(74) *Attorney, Agent, or Firm* — D. Kliger IP Services Ltd.

(57) ABSTRACT

Medical apparatus includes an endoscope, which includes a distal end configured for insertion into a body cavity and which includes an imaging assembly, configured to capture and output an image of a region of the body cavity in proximity to the distal end. An energy source is configured to emit pulses of energy through an energy guide. A control unit is configured to process the image so as to identify a target mass in the body cavity and to verify that an aiming beam directed through the energy guide is incident on the target mass and, responsively to so verifying, to actuate the energy source to direct a pulse of the energy via the energy guide onto the target mass.

7 Claims, 4 Drawing Sheets

(51) Int. Cl.
  *A61B 18/00* (2006.01)
  *A61B 18/20* (2006.01)
  *A61B 18/24* (2006.01)
  *A61B 18/18* (2006.01)
  *A61B 19/00* (2006.01)

(56) References Cited

U.S. PATENT DOCUMENTS

| | | | |
|---|---|---|---|
| 4,682,594 A * | 7/1987 | Mok | 606/7 |
| 4,763,652 A * | 8/1988 | Brisson | A61B 8/0833 601/4 |
| 4,887,605 A * | 12/1989 | Angelsen et al. | 600/439 |
| 4,939,336 A * | 7/1990 | Meyer et al. | 219/121.62 |
| 4,942,878 A | 7/1990 | Dory | |
| 4,984,575 A | 1/1991 | Uchiyama et al. | |
| 5,358,466 A | 10/1994 | Aida et al. | |
| 5,473,136 A * | 12/1995 | Engelhardt | B23K 26/032 219/121.62 |
| 5,531,739 A * | 7/1996 | Trelles | 606/2.5 |
| 5,643,250 A | 7/1997 | O'Donnell | |
| 5,697,885 A | 12/1997 | Konomura et al. | |
| 5,749,830 A * | 5/1998 | Kaneko et al. | 600/160 |
| 6,375,651 B2 | 4/2002 | Grasso et al. | |
| 6,454,761 B1 * | 9/2002 | Freedman | 606/5 |
| 7,967,016 B2 | 6/2011 | Anderson et al. | |
| 8,006,702 B2 | 8/2011 | Lin | |
| 8,235,968 B2 | 8/2012 | Tremaglio | |
| 8,414,472 B2 | 4/2013 | Hagelauer | |
| 8,535,250 B2 | 9/2013 | Owen et al. | |
| 8,535,293 B2 | 9/2013 | Faherty et al. | |
| 8,607,634 B2 | 12/2013 | Bailey et al. | |
| 8,659,646 B2 | 2/2014 | Adler et al. | |
| 8,753,332 B2 * | 6/2014 | Bragagna | A61B 18/20 606/13 |
| 2002/0103477 A1 | 8/2002 | Grasso, III et al. | |
| 2002/0119116 A1 | 8/2002 | Sahatjian et al. | |
| 2003/0149352 A1 | 8/2003 | Liang et al. | |
| 2004/0242961 A1 | 12/2004 | Bughici et al. | |
| 2004/0243123 A1 | 12/2004 | Grasso, III et al. | |
| 2005/0131339 A1 | 6/2005 | Makin et al. | |
| 2006/0020269 A1 | 1/2006 | Cheng | |
| 2006/0184076 A1 | 8/2006 | Gill et al. | |
| 2007/0016113 A1 | 1/2007 | Buchholtz et al. | |
| 2007/0016114 A1 | 1/2007 | Buchholtz et al. | |
| 2007/0021754 A1 | 1/2007 | Chernenko et al. | |
| 2007/0260112 A1 | 11/2007 | Rahmani | |
| 2008/0226029 A1 * | 9/2008 | Weir et al. | 378/65 |
| 2009/0275832 A1 | 11/2009 | Gelbart et al. | |
| 2009/0275866 A1 | 11/2009 | Gelbart et al. | |
| 2010/0092054 A1 | 4/2010 | Hensley et al. | |
| 2010/0185187 A1 | 7/2010 | Yamashita et al. | |
| 2011/0034832 A1 | 2/2011 | Cioanta et al. | |
| 2011/0054363 A1 | 3/2011 | Cain et al. | |
| 2011/0074943 A1 | 3/2011 | Modell et al. | |
| 2011/0082452 A1 | 4/2011 | Melsky et al. | |
| 2011/0257523 A1 | 10/2011 | Hastings et al. | |
| 2011/0257561 A1 | 10/2011 | Gertner | |
| 2011/0263967 A1 | 10/2011 | Bailey et al. | |
| 2012/0316396 A1 | 12/2012 | Robertson | |
| 2013/0072753 A1 | 3/2013 | Zappia et al. | |
| 2013/0102932 A1 | 4/2013 | Cain et al. | |
| 2013/0116561 A1 | 5/2013 | Rothberg et al. | |
| 2013/0211294 A1 | 8/2013 | Bohris | |
| 2014/0276101 A1 * | 9/2014 | Asselin et al. | 600/476 |
| 2014/0336497 A1 | 11/2014 | Gertner | |
| 2015/0055821 A1 | 2/2015 | Fotland | |
| 2015/0078615 A1 | 3/2015 | Staples, II et al. | |
| 2015/0213616 A1 | 7/2015 | Kappeler et al. | |

FOREIGN PATENT DOCUMENTS

| | | |
|---|---|---|
| CN | 1647774 A | 8/2005 |
| CN | 1695565 A | 11/2005 |
| DE | 4038295 A1 | 6/1992 |
| DE | 102006060070 A1 | 2/2008 |
| DE | 102009042276 A1 | 4/2011 |
| DE | 102011109069 A1 | 1/2013 |
| EP | 0194856 A2 | 9/1986 |
| EP | 0329492 A2 | 8/1989 |
| EP | 1882454 A2 | 1/2008 |
| EP | 1513463 B1 | 5/2011 |
| JP | H02161937 A | 6/1990 |
| JP | 0576539 A | 3/1993 |
| JP | H0584253 A | 4/1993 |
| JP | 05228158 A | 9/1993 |
| JP | H05285159 A | 11/1993 |
| JP | H0686782 A | 3/1994 |
| JP | 06217986 A | 8/1994 |
| JP | 4982638 B2 | 7/2012 |
| WO | 9214415 A2 | 9/1992 |
| WO | 9406380 A1 | 3/1994 |
| WO | 2005037062 A2 | 4/2005 |
| WO | 2011133922 A2 | 10/2011 |
| WO | 2013145708 A1 | 10/2013 |
| WO | 2013154708 A1 | 10/2013 |

OTHER PUBLICATIONS

MEDSOLUTION—an operating division of Medical Tourism Inc., "Lithotripsy", 4 pages, 2008 http://www.medsolution.com/surgery_urogen-lithotripsy.asp.

Waingankar et al., "Guidewires and Angled Catheters",Springer Science+Business Media New York, pp. 127-136, 2013.

Orkisz et al., "Image Based Renal Stone Tracking to Improve Efficacy in Extracorporeal Lithotripsy", The Journal of Urology, vol. 160, Issue 4, pp. 1237-1240, Oct. 1998.

International Application # PCT/US14/58147 Search Report dated Jan. 29, 2015.

International Application # PCT/US2015/026572 Search Report dated Jun. 12, 2015.

International Application # PCT/US2015/026571 Search Report dated Jun. 16, 2015.

U.S. Appl. No. 14/274,726 Office Action dated Sep. 2, 2015.

* cited by examiner

AIMING BEAM DETECTION FOR SAFE LASER LITHOTRIPSY

FIELD OF THE INVENTION

The present invention relates generally to minimally-invasive medical devices and procedures, and particularly to an apparatus and method to control targeted energy procedures that use an endoscope.

BACKGROUND

Laser lithotripsy is a minimally-invasive procedure that is widely used in remove stones from the urinary tract, including the urethra, bladder, ureters and kidneys. In order to perform laser lithotripsy, an endoscope (such as a cystoscope, ureteroscope or renoscope) is inserted into the urinary tract to the stone location, and an optical fiber is introduced into the working channel of the endoscope. The fiber is pushed forward until it exits the distal opening of the working channel and comes into close proximity with the stone. A laser beam is fired through the fiber onto the stone, causing the stone to absorb the laser beam energy and disintegrate.

If the laser beam is fired while the fiber is still inside the working channel of the endoscope, rather than protruding out of the distal opening, the beam can damage the working channel, as well as surrounding tissues. Various solutions to this problem have been proposed. For example, U.S. Patent Application Publication 2013/0072753 describes a system for preventing inadvertent actuation of a medical device. The system includes an elongate tube having a proximal end, a distal end, and a lumen extending from the proximal end to the distal end. The lumen is configured to receive a medical device having an actuated state and an inactive state. A detection system determines the position of the distal end of the medical device relative to the distal end of the elongate tube and controls the activation of the medical device.

SUMMARY

Embodiments of the present invention that are described hereinbelow provide methods and apparatus that may be used to control energy emission in endoscopic procedures.

There is therefore provided, in accordance with an embodiment of the present invention, medical apparatus, including an endoscope, which includes a distal end configured for insertion into a body cavity and which includes an imaging assembly, configured to capture and output an image of a region of the body cavity in proximity to the distal end. The apparatus includes an energy guide and an energy source, configured to emit pulses of energy through the energy guide. A control unit is configured to process the image so as to identify a target mass in the body cavity and to verify that an aiming beam directed through the energy guide is incident on the target mass and, responsively to so verifying, to actuate the energy source to direct a pulse of the energy via the energy guide onto the target mass.

In some embodiments, the apparatus includes an illumination source, which is configured to direct the aiming beam through the energy guide.

In some embodiments, the energy guide passes through the endoscope to an opening at the distal end. Typically, the endoscope includes a working channel, passing through the endoscope to the opening at the distal end, and the energy guide is configured for insertion through the working channel. The energy guide may be configured to protrude through the opening at the distal end of the endoscope, so that a distal tip of the energy guide is in proximity to the target mass. In a disclosed embodiment, the endoscope is configured for insertion through a urinary tract of a patient, wherein the target mass is a stone, and wherein the pulses emitted by the energy source are configured to be absorbed by and thereby induce disintegration of the stone.

Typically, the energy guide includes an optical fiber, and the energy source includes a laser.

In a disclosed embodiment, the control unit is configured to inhibit operation of the energy source when the aiming beam does not appear in the image to be incident on the target mass. Optionally, the control unit may be configured to delay inhibition of the operation of the energy source during a predefined time interval following emission of the pulse of energy onto the target mass.

There is also provided, in accordance with an embodiment of the present invention, a method for performing an endoscopic procedure, which includes providing an endoscope, which includes a distal end configured for insertion into a body cavity, and an energy guide, configured for insertion into the body cavity. An aiming beam is directed through the energy guide into the body cavity. An image of a region of the body cavity in proximity to the distal end is captured and is processed, using an image processor, so as to identify a target mass in the body cavity and to verify that the aiming beam is incident on the target mass. Responsively to so verifying, an energy source is actuated to direct a pulse of energy via the energy guide onto the target mass.

The present invention will be more fully understood from the following detailed description of the embodiments thereof, taken together with the drawings in which:

DETAILED DESCRIPTION OF EMBODIMENTS

Figure 1:
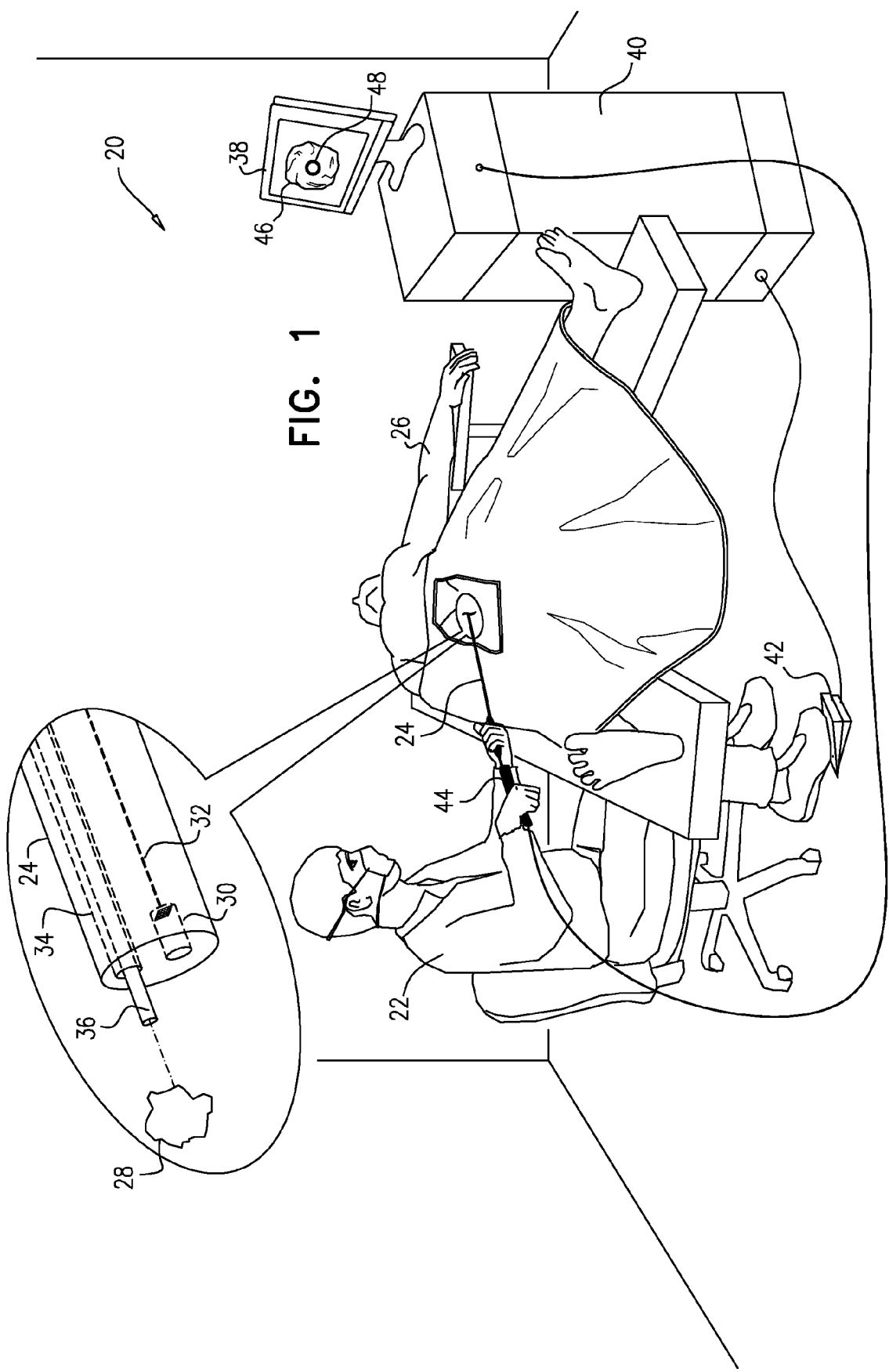
FIG. 1 is a schematic, pictorial illustration showing a system for laser lithotripsy, in accordance with an embodiment of the present invention.

It is believed that laser lithotripsy systems are known in the art and typically use a high-power infrared laser, such as a holmium YAG laser, to generate energy pulses that are fired at the target stone. It is also believed that the laser beam used for breaking the stone is typically invisible to the human eye and to standard image sensors, and thus another illumination source, such as a visible LED or laser source, may be used to generate a visible aiming beam. This aiming beam typically may be directed through an optical fiber or other similar device and arranged to strike the target of the laser beam. With the use of the aiming beam, an aiming beam spot can appear in the images formed when an endoscope is being used to view the target area and thus enables the physician operating the system to see where the energy from the fiber will be incident.

In order to avoid damage to surrounding tissues, the physician should make sure that the aiming beam is incident on the stone before firing the laser. Proper observation of the aiming beam spot on the stone should also help prevent misfiring of the laser while the fiber is still inside the working channel, rather than protruding out distally toward the target as it should be. In practice, however, stones tend to move during treatment, and maneuvering the endoscope and the fiber is difficult, requiring substantial dexterity and care. As a result, misfires occur all too commonly, resulting in damage to patient tissues and to the endoscope.

Embodiments of the present invention that are described hereinbelow are intended to prevent misfiring of the laser by verifying that the aiming beam is properly incident on the target stone before allowing the laser to be actuated. One way this objective may be accomplished by processing images captured by the endoscope camera. In addition to the benefits of preventing damage to tissues and equipment, this approach may be particularly advantageous in that it can be implemented simply by adding the appropriate processing and control capabilities to existing laser lithotripsy systems, without substantial modifications or additions to the system hardware.

Thus, in the disclosed embodiments, an endoscope, having a distal end configured for insertion into a body cavity, comprises one or more of the following:
An imaging assembly, which captures and outputs an image of a region of the body cavity in proximity to the distal end;
An energy guide, which may or may not pass through the endoscope to an opening or the area at the distal end of the endoscope; and
An energy source, which is coupled to emit pulses of energy through the energy guide.

In addition, as noted earlier, an illumination source may direct an aiming beam through the energy guide. Alternatively, assuming the energy source to comprise a laser, this laser may be configured to emit a low-power visible beam, in addition to the high-power energy pulses, for use as the aiming beam instead of a separate illumination source.

A control unit processes the image that is output by the imaging assembly so as to identify a target mass, such as a stone, in the body cavity and to verify that the aiming beam is incident on the target mass. On the basis of this verification, the control unit actuates the energy source to direct an energy pulse via the energy guide onto the target mass. Otherwise, the control unit may inhibit operation of the energy source.

In an embodiment described below, the endoscope comprises a working channel, the energy guide comprises an optical fiber, and the energy source comprises a laser. The optical fiber is inserted through the working channel as described above, so that the distal tip of the fiber protrudes from the distal opening of the working channel, in proximity to the target mass. The endoscope is configured for insertion through a urinary tract of a patient, wherein the pulses emitted by the laser are absorbed by and thereby induce disintegration of a stone, such as a kidney stone.

Although the embodiments described below make reference, by way of example, to laser lithotripsy in particular, the principles of the present invention are by no means limited to this specific therapeutic context. Rather, in alternative embodiments, the methods of image processing and control that are described herein may be applied, mutatis mutandis, in other sorts of therapeutic procedures using not only lasers, but also energy sources of other types, such as acoustic or microwave sources. Furthermore, although these embodiments are directed specifically to treatment of the urinary tract, the systems and methods described herein may similarly be applied in endoscopic treatments within other body cavities, such as the intestinal tract, the respiratory system, and the cardiovascular system, as well as elsewhere within the thoracic and abdominal cavities and in neurosurgical and dental procedures, or anywhere else in the body where a laser or other targeted energy source may be used.

FIG. 1 is a schematic, pictorial illustration showing a system 20 for laser lithotripsy, in accordance with an embodiment of the present invention. A system operator 22, typically a physician, such as a urologist, passes the distal end of a suitable endoscope 24 into a body cavity of a patient 26, such as into the bladder, ureter or kidney. As shown in the inset, operator 22 manipulates endoscope 24 in order to bring the distal end of the endoscope into proximity with a target mass, such as a stone 28.

An imaging assembly 30 in the distal end of the endoscope, comprising an image sensor and suitable imaging optics, as are known in the art, captures images of a region within the body cavity in the vicinity of the distal end and transmits corresponding image signals via wires 32 to a control console 40. Alternatively, the imaging assembly may comprise a fiberoptic image guide (not shown), which conveys images of the region to an image sensor at the proximal end of the endoscope. Typically, imaging assembly 30 also comprises an illumination source, as is known in the art, for illuminating the region of the captured image, but this element is likewise omitted from the figures for the sake of simplicity.

Endoscope 24 contains a working channel 34, extending from the proximal to the distal end of the endoscope. Operator 22 inserts an energy guide, typically a suitable optical fiber 36, through working channel 34 until the distal end of the optical fiber protrudes through the distal opening of the working channel, into proximity with stone 28. Both the high-power infrared laser beam that is used to disintegrate stone 28 and the visible aiming beam pass through fiber 36 from console 40 to the distal end of the fiber, where they are incident on stone 28 (as long as endoscope 24 is properly aimed).

Figure 2:
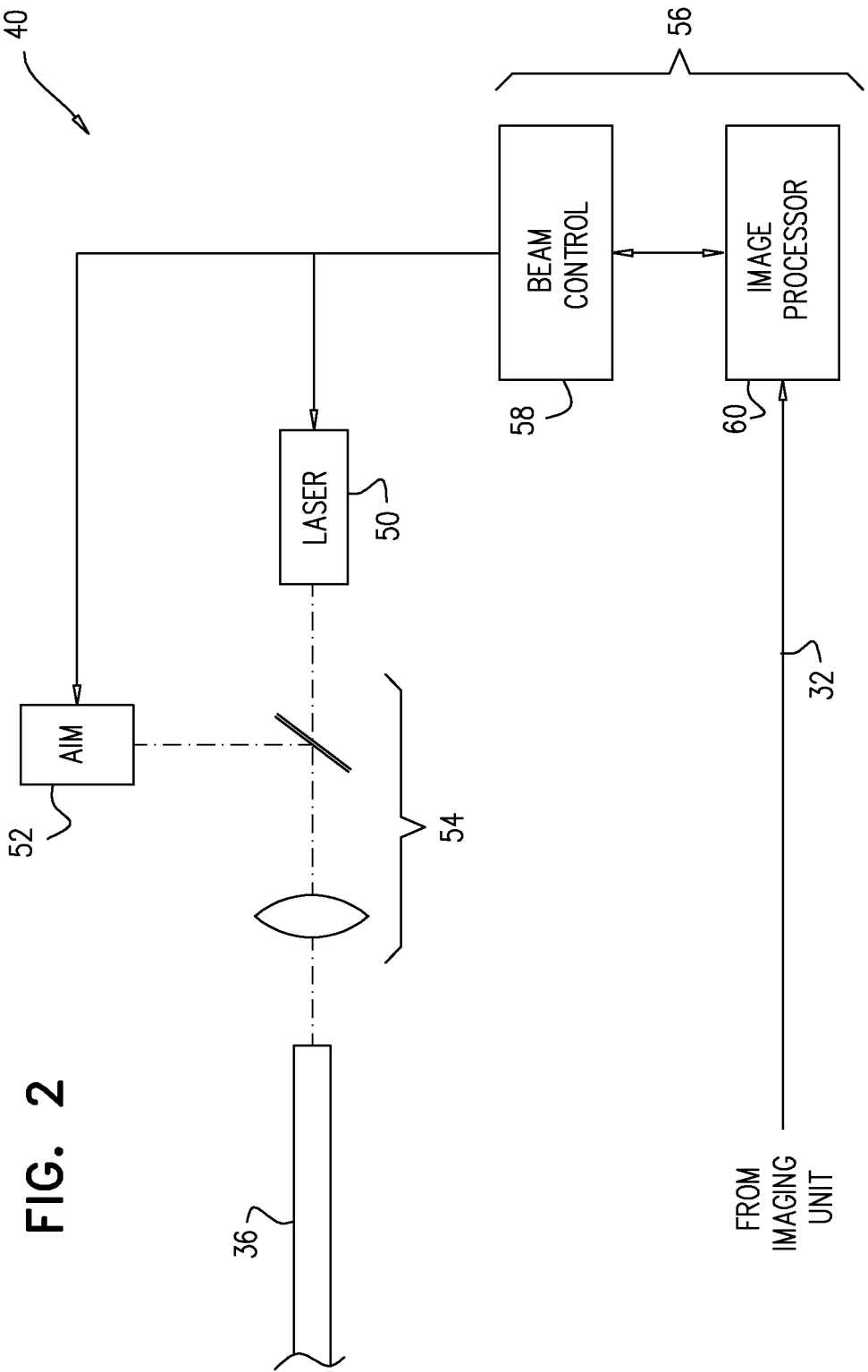
FIG. 2 is a block diagram that schematically shows elements of a control console in a laser lithotripsy system, in accordance with an embodiment of the present invention.

Console 40 comprises control and irradiation components, which are shown in FIG. 2. Operator 22 may interact with these components via suitable user interface elements, such as a foot pedal 42 and/or controls on a handle 44 of endoscope 24. Console 40 provides information to operator 22 on a display 38, and possibly also by other means, such as audio and/or haptic outputs. Typically, display 38 shows images captured by imaging assembly 30, which in this case include an image 46 of stone 28. When fiber 36 is properly deployed out of the distal end of working channel 34 and aimed at stone 28, the aiming beam will form a bright spot on the stone, which will appear as a beam spot 48 on image 46. Spot 48 may be recognized by its characteristic size, shape and color (for example, green).

FIG. 2 is a block diagram that schematically shows elements of console 40, in accordance with an embodiment of the present invention. A pulsed beam of a suitable laser 50, such as a holmium YAG laser, is aligned and directed by optics 54 into the proximal end of fiber 36. An illumination source 52, such as a visible LED- or laser-based source, emits an aiming beam, which is similarly focused by optics 54 into fiber 36. Alternatively, as noted earlier, laser 50 may be configured to emit a low-power visible beam, in addition to the high-power lithotripsy pulses, for use as the aiming beam, in which case illumination source 52 may not be needed.

A control unit 56 monitors and controls the operation of laser 50 and illumination source 52. Typically, control unit 56 comprises a general-purpose programmable processor with suitable interfaces and software for performing the functions that are described herein. Alternatively or additionally, some or all of these functions may be performed by a digital signal processor and/or by programmable or hard-wired hardware logic. Although in FIG. 2 and in the description that follows, control unit 56 is shown as comprising certain particular functional blocks, in practice these blocks may be implemented within a single device, such as an integrated circuit chip or as software modules running on a microprocessor. Furthermore, control unit 56 may typically perform other functions, as well, within console 40, such as operating the user interface of system 20, along with other operations that are beyond the scope of the present description.

Control unit 56 comprises an image processor 60, which processes the images output by imaging assembly in order to identify image 46 of stone 28 and to verify that spot 48, corresponding to the aiming beam, appears on image 46 in a manner indicating that the aiming beam is incident on the stone. Image processor 60 signals a beam controller 58, which actuates laser 50 on command of operator 22. Typically, controller 58 will allow laser 50 to be actuated only when image processor 60 provides an "enable" signal, after verifying that the aiming beam is incident on stone 28, and may inhibit actuation of the laser otherwise.

Figure 3:
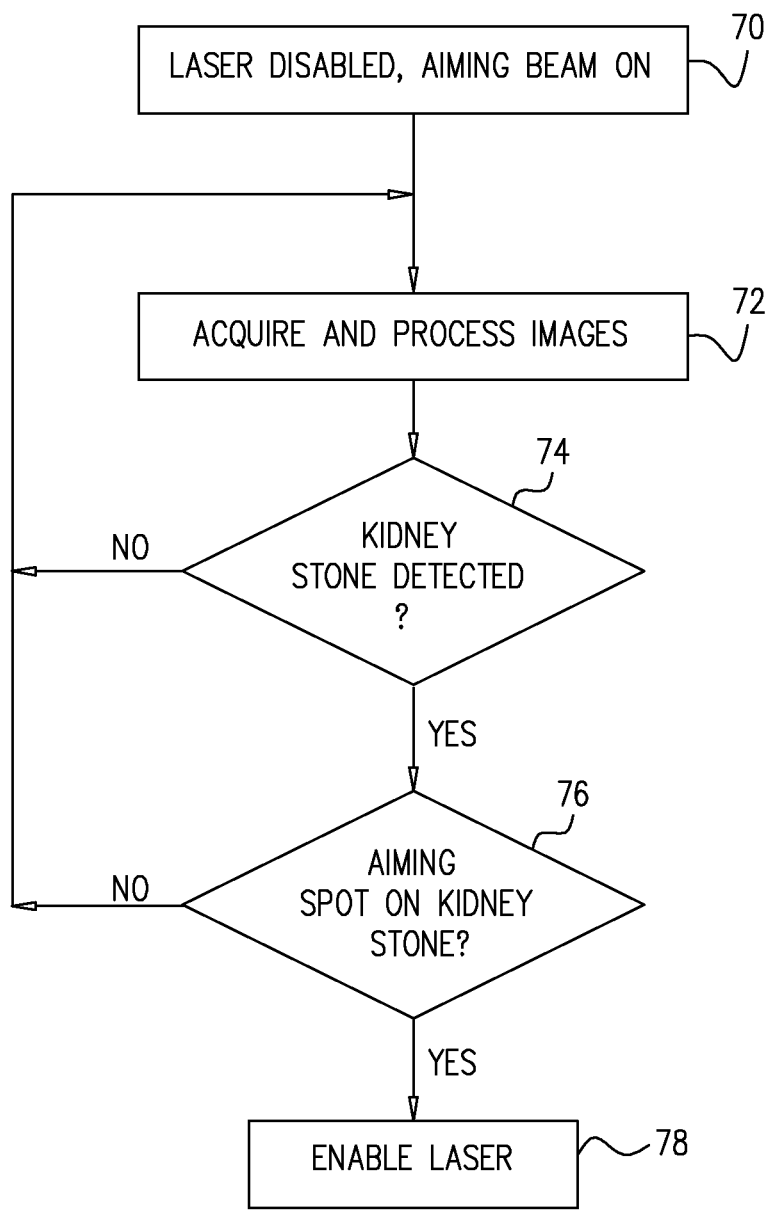
FIG. 3 is a flow chart that schematically illustrates a method for control of a lithotripsy procedure, in accordance with an embodiment of the present invention.

FIG. 3 is a flow chart that schematically illustrates a method for control of a lithotripsy procedure in system 20, in accordance with an embodiment of the present invention. This method is described here, for the sake of clarity and convenience, with reference to lithotripsy of kidney stones using system 20, but it may similarly be applied, mutatis mutandis, in other sorts of endoscopic systems and procedures.

Initially, until endoscope 24 and fiber 36 reach their proper positions within the patient's body, controller 58 keeps laser 50 disabled, while illumination source 52 is turned on to generate the aiming beam, at a preparatory step 70. Controller 58 or image processor 60 may verify at this stage that the illumination source is operational by optical or electronic means. Control unit 56 maintains this initial configuration of the laser and aiming beam while operator 22 advances endoscope 24 into the target organ, for example, the kidney, locates stone 28 within the organ (typically by observing display 38), and advances fiber 36 so that the distal end of the fiber is in proximity to stone 28.

Image processor 60 acquires and processes images that are output by imaging assembly 30, at an image processing step 72. Control unit 56 may perform this function continuously, while system 20 is in operation, or it may initiate the function when operator 22 initiates actuation of laser 50. Image processor 60 attempts to identify a stone in the acquired images, at a stone detection step 74. Various methods of image processing that are known in the art, such as pattern recognition techniques, may be used for this purpose.

For example, image processor 60 may perform the following operations in step 74:
1) The image is pre-processed to remove artifacts and spurious elements, which may otherwise decrease the efficiency of the detection process.
2) The image is divided into regions, each of which is a candidate to contain the stone. The regions may be defined by passing a sliding window over the image, or using methods of image segmentation.
3) Each image region is transformed to a vector in feature space in order to distinguish areas containing the stone from the background. The feature space may include values of properties such as color, texture, and edge contours. Prior, offline analysis is used to establish the boundaries of the area or areas in feature space into which stones may fall.
4) A classifier compares the feature space vectors to the boundaries of the stone areas, and thus decides which, if any, of the regions of the current image contains a stone. The classifier may simply compare each feature value to an applicable threshold, or it may perform a more complex, multivariate and/or statistical comparison.

If after the above analysis, image processor 60 concludes that the current image does not contain a stone, control unit 56 may signal operator 22 to indicate that the endoscope should be repositioned. For example, console 40 may provide a visual indication (such as the words "NO STONE IDENTIFIED" or "LASER DISABLED," or a corresponding icon) on display 38 and/or an audio output. In this case, system 20 continues to acquire and process new images at step 72, and laser 50 remains disabled.

On the other hand, if a stone is identified in the image at step 74, image processor 60 goes on to verify that spot 48 is properly located on image 46 of the stone, at an aiming verification step 76. Spot 48 may be detected on the basis of its distinctive, known color, as well as its shape and its location in the frame relative to the previous frame (based on the assumption that the location of the aiming beam changes in a continuous manner from frame to frame). Again, if image processor 60 does not detect the aiming spot on the stone image that was found at the preceding step, control unit 56 may signal operator 22 accordingly and return to step 72. Upon verifying that the aiming beam is properly located on stone 28, however, image processor 60 will signal beam controller 58 to enable laser 50, and the laser will fire a pulse onto the target.

Frequently, just after a laser pulse is incident on the surface of stone 28, a cloud of dust and debris accumulates between the stone and the distal end of endoscope 24. This cloud may obscure the images captured by imaging assembly 30 for several seconds, until the region of the stone is cleared by irrigation fluid from the endoscope. During this period, image processor 60 may be partially or completely unable to identify the stone and the aiming beam. In this sort of situation, control unit 56 may be programmed to enable repeated actuation of laser 50 for a short time following the initial laser pulse, even though the aiming beam cannot be visualized. Thus, beam controller 58 may not immediately inhibit laser 50 when image processor 60 loses the image of the stone after the initial laser pulse, but rather may delay such inhibition for a predefined time interval so that the laser beam is inhibited only if the loss of image persists for a certain length of time.

Figure 4:
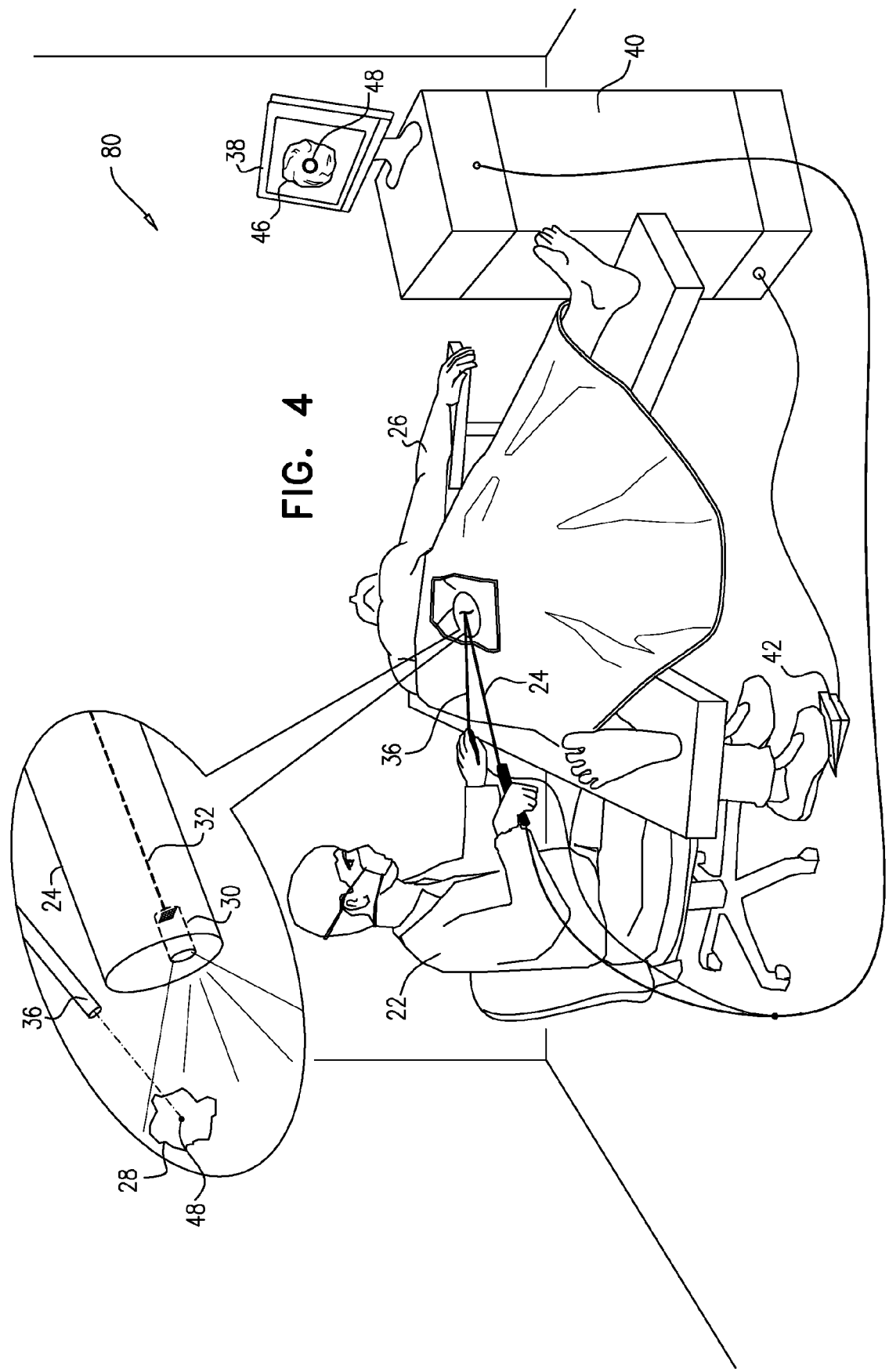
FIG. 4 is a schematic, pictorial illustration showing a system for laser lithotripsy, in accordance with another embodiment of the present invention.

FIG. 4 is a schematic, pictorial illustration showing a system 80 for laser lithotripsy, in accordance with an alternative embodiment of the present invention. The operation of this embodiment is similar to that of system 20 (FIG. 1), and like elements in FIG. 4 are labeled with the same numbers as in FIG. 1. In system 80, however, optical fiber 36 is separate from endoscope 24 and is manipulated by operator 22 independently. (This sort of arrangement may be used, for example, in laparoscopic procedures. Fiber 36 in this case is typically connected by its own cable to console 40, but this cable is omitted from FIG. 4 for the sake of simplicity.)

As in the preceding embodiment, operator 22 of system 80 manipulates both endoscope 24 and fiber 36 so that imaging assembly 30 captures an image of stone 28, and so that beam spot 48 appears on the stone. When these conditions are fulfilled, laser 50 may be actuated to fire a laser pulse toward the stone, as described above.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Medical apparatus, comprising:
    an endoscope, which comprises a distal end configured for insertion into a body cavity and which comprises an imaging assembly, configured to capture and output an image of a region of the body cavity in proximity to the distal end;
    an energy guide;
    an energy source, configured to emit pulses of energy through the energy guide; and
    a control unit, which is configured to process the image so as to identify a target mass in the body cavity and to verify that an aiming beam directed through the energy guide is incident on the target mass and, responsively to so verifying, to actuate the energy source to direct a pulse of the energy via the energy guide onto the target mass,
    wherein the control unit permits repeated actuation of the energy source even when the aiming beam does not appear in the image to be incident on the target mass, so that the energy source continues to direct further pulses of the energy via the energy guide for a predefined time interval following emission of the pulse of energy onto the target mass and then, after the predefined time interval, inhibits operation of the energy source when the aiming beam still does not appear in the image to be incident on the target mass.

2. The apparatus according to claim 1, and comprising an illumination source, which is configured to direct the aiming beam through the energy guide.

3. The apparatus according to claim 1, wherein the energy guide passes through the endoscope to an opening at the distal end.

4. The apparatus according to claim 3, wherein the endoscope comprises a working channel, passing through the endoscope to the opening at the distal end, and wherein the energy guide is configured for insertion through the working channel.

5. The apparatus according to claim 4, wherein the energy guide is configured to protrude through the opening at the distal end of the endoscope, so that a distal tip of the energy guide is in proximity to the target mass.

6. The apparatus according to claim 4, wherein the endoscope is configured for insertion through a urinary tract of a patient, wherein the target mass is a stone, and wherein the pulses emitted by the energy source are configured to be absorbed by and thereby induce disintegration of the stone.

7. The apparatus according to claim 1, wherein the energy guide comprises an optical fiber, and wherein the energy source comprises a laser.

* * * * *